United States Patent
Heymann et al.

(10) Patent No.: US 9,650,274 B2
(45) Date of Patent: May 16, 2017

(54) METHOD AND INSTALLATION FOR PROCESSING RAW LIQUID MANURE AND/OR FERMENTATION RESIDUES FROM BIOGAS PRODUCTION

(71) Applicant: GEA Mechanical Equipment GmbH, Oelde (DE)

(72) Inventors: Sven Heymann, Sangerhausen (DE); Bernd Lueking, Guetersloh (DE)

(73) Assignee: GEA Mechanical Equipment GmbH, Oelde (DE)

( * ) Notice: Subject to any disclaimer, the term of this patent is extended or adjusted under 35 U.S.C. 154(b) by 204 days.

(21) Appl. No.: 14/383,383

(22) PCT Filed: Feb. 28, 2013

(86) PCT No.: PCT/EP2013/053992
§ 371 (c)(1),
(2) Date: Sep. 5, 2014

(87) PCT Pub. No.: WO2013/131798
PCT Pub. Date: Sep. 12, 2013

(65) Prior Publication Data
US 2015/0041405 A1 Feb. 12, 2015

(30) Foreign Application Priority Data

Mar. 6, 2012 (DE) .................. 10 2012 004 497

(51) Int. Cl.
*C02F 9/00* (2006.01)
*C12M 1/00* (2006.01)
(Continued)

(52) U.S. Cl.
CPC ............. *C02F 9/00* (2013.01); *C02F 1/38* (2013.01); *C02F 1/52* (2013.01); *C02F 1/66* (2013.01);
(Continued)

(58) Field of Classification Search
CPC ...... C02F 9/00; C02F 1/52; C02F 1/66; C02F 1/38; C12M 47/08; C12M 1/00; C12M 47/00; C12M 47/12; C12M 47/10
See application file for complete search history.

(56) References Cited

U.S. PATENT DOCUMENTS

| 2003/0084693 A1* | 5/2003 | Sower | C05F 3/00 71/11 |
|---|---|---|---|
| 2008/0093292 A1* | 4/2008 | Zotter | C02F 1/36 210/603 |
| 2008/0250723 A1* | 10/2008 | Fragiacomo | B01D 3/00 51/298 |

FOREIGN PATENT DOCUMENTS

| DE | 40 27 581 A1 | 3/1992 |
|---|---|---|
| DE | 10 2006 057 163 A1 | 6/2008 |

(Continued)

OTHER PUBLICATIONS

International Search Report (PCT/ISA/220 and PCT/ISA/210) dated Jul. 22, 2013 with English translation (11 pages).
(Continued)

*Primary Examiner* — Chester Barry
(74) *Attorney, Agent, or Firm* — Crowell & Moring LLP

(57) ABSTRACT

A method for processing raw liquid manure and/or fermentation residues involves providing raw liquid manure and/or fermentation residues, purifying the raw liquid manure and/or fermentation residues in a first purification stage so as to form a first solid phase and a first purified liquid phase, pre-conditioning the first purified liquid phase in order to separate ultrafine particles from the first purified liquid phase, and purifying the first purified liquid phase in a second purification stage so as to form a second solid phase and a second purified liquid phase.

17 Claims, 1 Drawing Sheet

(51) Int. Cl.
*C02F 1/38* (2006.01)
*C02F 1/52* (2006.01)
*C02F 1/66* (2006.01)
*C02F 103/20* (2006.01)

(52) U.S. Cl.
CPC ............ *C12M 47/00* (2013.01); *C12M 47/08* (2013.01); *C12M 47/10* (2013.01); *C12M 47/12* (2013.01); *C02F 2103/20* (2013.01); *Y02E 50/343* (2013.01); *Y02W 30/47* (2015.05)

(56) References Cited

FOREIGN PATENT DOCUMENTS

| | | |
|---|---|---|
| EP | 1 013 614 A1 | 6/2000 |
| WO | WO 2004/015120 A1 | 2/2004 |
| WO | WO 2005/105680 A1 | 11/2005 |
| WO | WO 2010/074953 A1 | 7/2010 |
| WO | WO 2011/038364 A1 | 3/2011 |

OTHER PUBLICATIONS

German-language Written Opinion (PCT/ISA/237) dated Jul. 22, 2013 (16 pages).

* cited by examiner

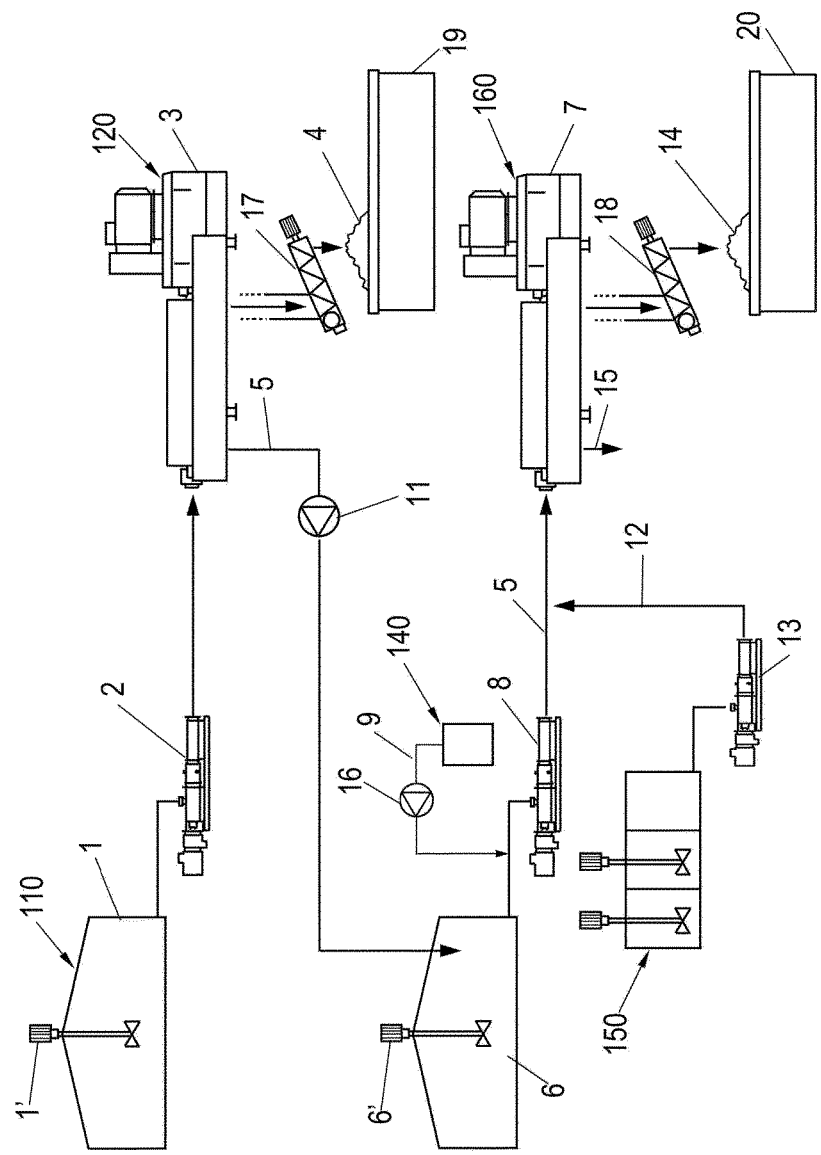

METHOD AND INSTALLATION FOR PROCESSING RAW LIQUID MANURE AND/OR FERMENTATION RESIDUES FROM BIOGAS PRODUCTION

BACKGROUND AND SUMMARY OF THE INVENTION

Exemplary embodiments of the invention relate to a method and an installation for processing raw liquid manure and/or fermentation residues from biogas production.

It is known that a solid phase and a treated liquid phase are produced in the separation of raw liquid manure and/or fermentation residues with a solid bowl scroll centrifuge. While in the separation of raw liquid manure the solid phase can be utilized, for example for biogas production, it would be desirable to further simplify the disposal of the treated liquid phase. In accordance with the invention this would be possible if the liquid phase were to contain still less suspended matter and ultrafine particles and the COD value (chemical oxygen demand) of the treated liquid phase could be lowered. According to the state of the art such treatment has hitherto not been possible, or only with very high expenditure, and accordingly exemplary embodiments address such deficiencies of conventional techniques.

Accordingly, exemplary embodiments of the present invention are directed to a method and a device for processing raw liquid manure and/or fermentation residues from biogas production, which allows simpler disposal of the treated liquid phase.

According to the invention, a method for processing raw liquid manure and/or fermentation residues comprises the following steps: provision of raw liquid manure and/or of fermentation residues; treatment of the raw liquid manure and/or the fermentation residues in a first treatment stage with formation of a first solid phase and a first treated liquid phase; preconditioning of the first treated liquid phase; and treatment of the first treated and preconditioned liquid phase in a second treatment stage with formation of a second solid phase and a second, further treated liquid phase.

Through the further removal of the ultrafine particles or suspended matter as a result of the preconditioning, the COD content of the second treated liquid phase compared to the first treated liquid phase is lowered so far that introduction into a biological stage of a treatment plant becomes possible. The COD value (chemical oxygen demand, particularly in mg/l) is a measure of the sum of all organic compounds in water, including the compounds difficult to degrade.

Here the preconditioning can advantageously and simply be effected in the first step by addition of a flocculant and/or alteration of the pH. This serves for the formation of larger solid particles by flocculation.

Also, during the addition of the flocculant it is advantageous if in the second step a further addition of a flocculation aid is effected to improve the shear strength of a coagulate. Due to the better shear strength, the coagulate can also be exposed to higher centrifugal forces and be better separated from the first (pre-)treated liquid phase by a further treatment process.

It is advantageous if the treatment of raw liquid manure or the fermentation residues in the first treatment stage in step ii) is effected by a centrifuge, in particular a solid bowl scroll centrifuge. Admittedly, a screw press can also be used for dewatering the raw liquid manure. However, it has been found that slimes can be particularly effectively removed from the clarified phase through the use of a centrifuge, whereas with use of screw press, these slimes predominantly remain in the first treated liquid and complicate its treatment in the second treatment stage.

In order to facilitate the biological degradability of the second solid phase, it is advantageous if the flocculation aid is a water-based polymer.

The first solid phase obtained in step ii) can be used for example for the production of biogas or as a phosphate-rich manure.

The second treated liquid phase advantageously has a decreased COD value relative to the first treated liquid phase. A low COD value of a liquid results in a lower burden on its introduction into a treatment plant. The second solid phase can also be used in many ways, such as again for biogas production or as phosphate-rich manure.

According to the invention, an installation for processing raw liquid manure and/or fermentation residues comprises at least one first centrifuge, in particular a solid bowl scroll centrifuge, for dewatering raw liquid manure with formation of a first treated liquid phase and a first solid phase and a first metering device for the addition of a flocculating agent to the first treated liquid phase or an agent for altering the pH of the first treated liquid phase.

The addition of a flocculant to raw liquid manure is already known. However, such an addition raises the chemical burden of the first solid phase. Apart from this, in spite of the addition of a flocculant, there is often a considerable content of ultrafine particles in the first treated liquid phase. On the other hand, the addition of the flocculant or a means for altering the pH to the first treated liquid phase, i.e. only after the first treatment stage, enables the obtention of a very largely ultrafine particle-free clarified phase by mechanical treatment in a second treatment stage.

BRIEF DESCRIPTION OF THE DRAWING FIGURES

Below, a preferred practical example is explained in more detail on the basis of the drawing.

FIG. 1 shows a schematic representation of an installation and a method for processing raw liquid manure, which can however also be used in the same manner on fermentation residues from biogas production.

DETAILED DESCRIPTION

Referring now to FIG. 1, according to the method according to the invention, raw liquid manure (which has for example a COD value of about 40000) or fermentation residues (which have for example a COD value of 60000) from a biogas plant is first collected in a first tank 1. In order to obtain as uniform a viscosity as possible and as far as possible avoid settling of solids, the tank 1 preferably contains a stirring device 1'.

From the first tank 1, the accumulated raw liquid manure is passed via a conveyor pump 2 into a first centrifuge 3, preferably a solid bowl scroll centrifuge. In this first centrifuge 3 in a first treatment stage 120, a treatment into a first solid phase 4 and a first treated liquid phase 5 is effected.

Here the first solid phase is passed, for example, via a screw conveyor 17 into a collecting vessel 19.

The first treated liquid phase 5 is passed, via a pump 11, into a second tank 6 and collected there. This second tank 6 also preferably has a stirring device 6' in order to achieve as uniform as possible a viscosity of the collected first treated liquid phase 5.

From the second tank 6, the first treated liquid phase 5 is pumped into a second centrifuge 7 by means of a third conveyor pump 8.

It is advantageous if the flocculant 9 is added to first treated liquid phase in the preconditioning. As the flocculant, PAC (polyaluminum chloride) or $FeCl_3$ (iron(III) chloride) are especially suitable.

For this, a metered quantity of the flocculant 9 from, for example, a holding tank is metered in by means of a metering device (for example a pump 13). The preconditioning can take place during the transfer of the first treated liquid phase 5 from the first centrifuge 3 into the second tank 6 and/or directly in the second tank 6 and/or after the second tank before or at the latest during the further introduction into a treatment device such as a further centrifuge (which is explained in still more detail below).

Through the addition of flocculant 9, after a certain exposure time, coagulation of ultrafine components in the clarified phase into larger macroflocs takes place.

It is particularly advantageous if in addition to the addition of a flocculant 9, the addition of a flocculation aid 12 is also effected in order to increase the shear stability of the coagulate or of the macroflocs formed. Preferably but not obligatorily, the flocculation aid 12 is a mineral oil-free chemical, particularly preferably a water-based polymer, in order not to adversely affect environmental compatibility.

In the practical example represented in FIG. 1, the addition of the flocculation aid 12 is effected via a third conveyor pump 13 after the second tank 6.

Next, the first treated liquid phase 5 with the coagulated ultrafine components is passed directly or after a certain time period into a second centrifuge 7. In this second centrifuge 7, which is preferably also configured as a solid bowl scroll centrifuge, a further treatment of the first "pre"-treated liquid phase 5 takes place with formation of a second treated liquid phase 15, which can also be described as a clarified phase, and a second solid phase 14.

The second solid phase 14 is, for example, passed via one (or the same) screw conveyor 17 or 18 into one (or the same) collecting vessel 19 or 20.

With smaller volumes of raw liquid manure, after preconditioning has taken place and following the first treatment stage 120, the first treated liquid phase 5, can also be recycled into the first centrifuge 3 for the second treatment stage 160. Thus only a single centrifuge is required for processing of the treated liquid phase 5 by a two-fold treatment.

Below, on the basis of the practical example of FIG. 1, individual process steps in advantageous form are explained in more detail.

In the first tank 1, provision of raw liquid manure or fermentation residues 110 takes place. This provision can take place, for example, by collection of raw liquid manure in the tank 1. Alternatively, provision can for example also be effected by passing fermentation residues to the first centrifuge 3 directly after a fermentation process.

After the provision of raw liquid manure or fermentation residues 110, a treatment of raw liquid manure or the fermentation residues is effected in a first treatment stage 120. In this, the raw liquid manure or the fermentation residues are treated by means of the first centrifuge 5 with formation of a first treated liquid phase 5 and a first solid phase 6.

This treatment of raw liquid manure preferably takes place without chemical additives. In this first treatment stage 120, the solid is not maximally dewatered. This effects a separation of slimes, mainly phosphates, with the solid. A phosphate-rich solid is thus obtained, which can be disposed of or optionally also be used as manure because of the high nutrient concentration. Alternatively, because of its high biogas potential, this solid can also be used as a starting material in biogas plants.

In the first treatment stage 120, both a screw press and a centrifuge, in particular a solid bowl scroll centrifuge, preferably a decanter, can be used, use whereof is however preferred to use of a screw press.

For it has been found that the separation of the phosphate-containing slimes takes place only to a small extent with the use of screw presses, since with screw presses the raw liquid manure or fermentation residues are filtered, as a result of which only coarse components are removed from the clarified phase.

In contrast to this, the phosphate-containing slimes are almost completely removed from the clarified phase on centrifugal clarification in a decanter. Because of the reduction in slimes, the viscosity of the clarified phase compared to the raw liquid manure is advantageously lowered at the same time, so that the first treated liquid phase 5 after the first treatment stage 120, has approximately the viscosity of water. The first treated liquid phase 5 already still contains only ultrafine particles and suspended matter, has a low phosphate value and has the viscosity of water.

The treatment of raw liquid manure or the fermentation residues in a first treatment stage 120 is followed by the preconditioning of the first treated liquid phase 5 for clearing further ultrafine particles from the first treated liquid phase 5.

The preconditioning is preferably effected by metering in 130 of the flocculant 9 with formation of a coagulate. For further optimization of the coagulate, the metering in 140 of the flocculation aid can additionally also be effected, as a result of which the macroflocs formed acquire a higher shear stability.

An alternative version of the preconditioning of the first treated liquid phase 5 for removing ultrafine particles from the first treated liquid phase 5 is effected by a, preferably multistage, pH shift. In this, the pH of the first treated liquid phase is adjusted into the acidic range, preferably to a pH≤5.8, particularly preferably ≤5.5. In this slightly acidic range, the formation of the coagulate takes place in the form of hydroxide flakes, apparently because of a charge reversal at the isoelectric point. Particularly preferred here is a pH range greater than pH=3.8.

Following the preconditioning of the first treated liquid phase 5, for clearing ultrafine particles from the first treated liquid phase 5, the aforesaid treatment of the first treated liquid phase 5 is effected in the second treatment stage 150 with formation of the second treated liquid phase 15 and the solid phase 14.

If the preconditioning of the first treated liquid phase 5 is effected by shifting the pH, then it is advantageous if after the treatment in the second treatment stage 150 the pH is again raised to a value between 6.5 and 7.5.

The second treated liquid phase 15 formed in this manner presents very good preconditions for a biological stage or reverse osmosis. Thus, the COD value compared to phase 5 can once more be lowered markedly further to down to ca. 4000 (in the processing of raw liquid manure) or ca. 6000 (in the processing of fermentation residues). It can further for example be field-sprayed or applied via drag hoses, so that the nitrogen dissolved in the liquid is particularly effectively made available directly to the roots of plants largely without nitrogen losses.

The second treated solid phase 5 has relatively low DS values (dry substance values), since there is no longer any supporting framework in the residual solid due to the prior removal of coarse particles. In particular however, the second treated liquid phase 15 advantageously has a decreased COD value compared to the first treated liquid phase 5. It can be processes in various ways, thus it can be mixed with the phosphate-rich phase 4 and utilized together with this or disposed of.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF SYMBOLS

Tank 1
Stirring device 1'
Conveyor pump 2
Centrifuge 3
Solid phase 4
Liquid phase 5
Tank 6
Stirring device 6'
Centrifuge 7
Conveyor pump 8
Flocculant 9
Pump 10
Pump 11
Flocculation aid 12
Pump 13
Solid phase 14
Clarified phase 15
Provision of raw liquid manure and/or fermentation residues 110
First treatment stage 120
Addition of a flocculant 130
Addition of a flocculation aid 140
Second treatment stage 150

The invention claimed is:

1. A method for processing raw liquid manure and/or fermentation residues from biogas production, the method comprising:
   i) providing raw liquid manure and/or of fermentation residues;
   ii) treating the raw liquid manure and/or the fermentation residues in a first treatment stage to form a first solid phase and a first treated liquid phase;
   iii) preconditioning the first treated liquid phase; and
   iv) treating the first treated and preconditioned liquid phase in a second treatment stage to form a second solid phase and a second, further treated liquid phase or clarified phase.

2. The method of claim 1, wherein the treatment of raw liquid manure or the fermentation residues in the first treatment stage is performed by a first solid bowl scroll centrifuge.

3. The method of claim 2, wherein the treatment of the first treated and preconditioned liquid phase in the second treatment stage is performed by a second solid bowl scroll centrifuge or by recycling the first treated liquid phase into the first solid bowl centrifuge.

4. The method of claim 1, wherein the preconditioning is performed by adding a flocculant and/or by shifting the pH.

5. The method of claim 4, wherein the shifting of the pH takes place into an acidic range.

6. The method of claim 5, wherein the shifting of the pH is to a pH≤5.8.

7. The method of claim 5, wherein the shifting of the pH is to a pH≤5.5.

8. The method of claim 7, wherein after the treatment of the first treated and preconditioned liquid phase in the second treatment stage, according to step iv), the second, further treated liquid phase is adjusted to a pH≥6.5.

9. The method of claim 8, wherein the second, further treated liquid phase is adjusted to a pH range between 6.5 and 7.5.

10. The method of claim 4, wherein in addition to the addition of a flocculant, an addition of a flocculation aid is performed to improve the shear strength of a coagulate.

11. The method of claim 1, wherein the treatment in the first stage is effected such that the phosphate content of the first treated liquid phase is at most 20% of a phosphate content of the raw liquid manure.

12. The method of claim 1, wherein the treatment in the first stage is effected such that the phosphate content of the first treated liquid phase is at most 10% of a phosphate content of the raw liquid manure.

13. The method of claim 4, wherein the flocculant is PAC or FeCl3.

14. The method of claim 10, wherein the flocculation aid is a water-based polymer.

15. An installation for processing raw liquid manure and/or fermentation residues, the installation comprising:
   a) at least one first centrifuge, which is a solid bowl scroll centrifuge and is configured to dewater raw liquid manure and/or fermentation residues to form of a first treated liquid phase and a first solid phase;
   b) a first metering device configured to add a flocculant to the first treated liquid phase or an agent for altering the pH of the first treated liquid phase; and
   a tank configured to collect the first treated liquid phase, wherein the tank has a feed line from the first centrifuge and an outlet line which opens into the inlet of a second centrifuge or into the inlet of the first centrifuge.

16. The installation of claim 15, further comprising:
   a second metering device configured to add a flocculation aid into the first treated liquid phase.

17. The installation of claim 16, wherein the first and the second metering device are positioned on the tank for collection of the treated liquid phase, on the feed line of the first treated liquid phase, or on the outlet line of the first treated liquid phase.

* * * * *